United States Patent [19]
Archer et al.

[11] Patent Number: 4,948,790
[45] Date of Patent: Aug. 14, 1990

[54] LONG-ACTING ANDROGENIC COMPOUNDS AND PHARMACEUTICAL COMPOSITIONS THEREOF

[76] Inventors: Sydney Archer, Renesselaer Polytechnic Institute, Troy, N.Y. 12181; Gabriel Bialy, National Institute of Health, Bethesda, Md. 20892; Richard P. Blye, National Institute of Health, Bethesda, Md. 20892; Pierre Crabbe, deceased, late of Brussels; by Lucie Crabbe, executor, 14, Avenue Jules Cesar, 1150 Brussels, both of Belgium; Egon R. Diczfalusy, Reproductive Endocrinology Research Unit, Karolinska sjukhuset, 104 01 Stockholm 60, Sweden; Carl Djerassi, Department of Chemistry Stanford University, Palo Alto, Calif. 94305; Josef Fried, Department of Chemistry, University of Chicago, Chicago, Ill. 60637; Hyun K. Kim, National Institute of Health, Bethesda, Md. 20892

[21] Appl. No.: 89,391

[22] Filed: Aug. 26, 1987

[51] Int. Cl.$^5$ .......................... C07J 9/00; A61K 31/56
[52] U.S. Cl. ...................................... 514/178; 552/638
[58] Field of Search ............... 260/397.3, 397.4, 397.5, 260/397.4; 514/117.7, 178

[56] References Cited
U.S. PATENT DOCUMENTS 2,566,358  9/1951  Ott et al.
3,056,727 10/1962  Allais et al. ........................ 260/397.4
3,314,856  4/1967  Allais et al. ........................... 514/178
3,433,813  3/1969  Boswell et al. .................... 260/397.4
4,147,783  4/1979  Van Der Vies ..................... 514/171

OTHER PUBLICATIONS

Bischoff et al., J. Biol. Chem. 189:729–738 (1951) "Enzymatic Hydrolysis of Steroid Hormone Esters by Blood Serum".
Matlin S. A. et al., Chem. Abs., vol. 107 33296 "Long Acting Androgans" (1987).
Bundgaard H. "Design of Prodrugs" in 'Design of Prodrugs' Bundgaard H. ed.; Elsevier N.Y. (1985), pp. 2–4.
Ott et al.; J. Clin. Endocrinol. Metab. 12, 15–27 (1952); Testosterone –Cyclo-Pentylpropionate: A New Long-Lasting Androgen.
Gould et al.; J. Am. Chem. Soc. 79 4472–4475 (1957); Long-Acting Testosteron Esters. Some Consideration on Their Biological Utilization.
Weinbauer et al.; Acta Endocrinologica (COPENH) 1986, 113: 128–132; New Injectable Testosterone Ester Maintains Serum Testosterone of Castrated Monkeys in the Normal Range for Four Months.

Primary Examiner—H. M. S. Sneed
Assistant Examiner—James A. Saba
Attorney, Agent, or Firm—Cushman, Darby & Cushman

[57] ABSTRACT

Long-acting androgenic compositions comprising $C_4$–$C_6$ cycloalkyl carboxylic acids of testosterone and a pharmaceutically acceptable carrier medium. The ester can be dissolved in an acceptable oily medium or suspended in an aqueous medium in the form of micronised particles or in the form of milled particles.

15 Claims, 10 Drawing Sheets

LONG-ACTING ANDROGENIC COMPOUNDS AND PHARMACEUTICAL COMPOSITIONS THEREOF

BACKGROUND OF THE INVENTION

1. Technical Field

The invention relates, in general, to esters of testosterone possessing androgenic activity and, in particular, to new long-acting cycloalkyl carboxylic acid esters of testosterone and pharmaceutical compositions thereof.

2. Background Information

The need for androgenic substances in the practice of medicine is well documented. Androgens may be used for the replacement of the natural hormone testosterone in hypogonadism and following castration. Androgens are commonly employed to accelerate growth in childhood, promote anabolism, stimulate erythropoiesis. Androgens are also employed as a palliative for recurrent and metastatic carcinoma of the breast. Both oral and parenteral formulations of androgens are currently available.

Cycloalkyl esters of testosterone have been described by van der Vies (U.S. Pat. No. 4,147,783) for use as orally administered androgens. The cycloalkyl group of the esters disclosed contains 7–12 carbons and is optionally substituted by aliphatic groups containing 1–6 carbon atoms.

A number of testosterone cycloalkylalkanoates have been described by Ott et al. (*Journal of Clinical Endocrinology and Metabolism* 12, 15 (1952)); one cycloalkyl carboxylic acid ester, testosterone 4-bicyclohexylcarboxylate, being mentioned. Ott et al evaluated the compounds disclosed therein for long-acting androgenic activity following a single subcutaneous injection of an oily solution (cottonseed oil) in rats. Testosterone 4-bicyclohexylcarboxylate was found to be less potent than the testosterone propionate standard. These investigators also studied an aqueous microcrystalline suspension of testosterone, but the results were "disappointing" and both the intensity and duration of action were less than the standard, testosterone propionate (see also U.S. Pat No. 2,566,358, Ott to The Upjohn Company for testosterone β-cyclopentylopropionate).

Gould, et al. (*Journal of the American Chemical Society* 79, 4472 (1957)), disclosed a large number of testosterone esters including several substituted cyclohexanecarboxylates. Among the latter were the 2-, 3- and 4-methyl and 4-ethyl, propyl and isopropyl, and 3, 3, 5-trimethylcyclohexanecarboxylate. Most of these compounds exhibited a greater intensity, and all exhibited greater duration, of androgenic action than the standard employed, testosterone propionate. Unsubstituted testosterone cyclohexanecarboxylate and the corresponding 2-, 3-and 4-methyl substituted analogs were also administrated as aqueous suspensions and all were found to exhibit two to four times the duration of activity as that of the standard, testosterone propionate.

Weinbauer, et al. (*Acta Endocrinologica* (Copenh) 113, 128 (1986)), have reported the levels of testosterone and its metabolite, dihydrotestosterone, following a single intramuscular injection of an aqueous suspension of testosterone 17β-(trans- 4-n-butyl)cyclohexanecarboxylate or testosterone enanthate standard in sesame oil in orchidectomized cynomolgus monkeys. Both intensity and duration of elevated hormone levels were greater following administration of testosterone 17β-(trans-4-n-butyl) cyclohexanecarboxylate.

Thus, while oral and parenteral formulations of androgens are available, oral preparations require continual, daily self-medication and parenteral forms must be administered frequently to maintain physiological blood level. Compounds resulting from the esterification at position 17 of testosterone often exhibit enhanced duration of action following parenteral administration, however, many of the most potent of these drugs must be injected at weekly or biweekly intervals to maintain adequate therapeutic blood levels. In addition, many of these compounds produce high initial peak levels of testosterone which are in excess of normal physiological range.

SUMMARY OF THE INVENTION

It is a primary object of the invention to provide esters of testosterone, and pharmaceutical compositions thereof, capable of long-acting androgenic activity following parenteral administration to mammals.

It is a further object of the invention to provide a pharmaceutical composition comprising, as an active ingredient, an ester of testosterone in an amount sufficient to produce a relatively constant blood level of testosterone without causing initial high peak drug levels.

It is another object of the invention to provide a method for suppressing fertility in male mammals and t provide androgen replacement in those methods of male fertility control in which production of the natural hormones of the testis are compromised.

Further objects and advantages of the present invention will be apparent from the following detailed description of species thereof.

The foregoing objects of the present invention are achieved by providing novel cycloalkyl carboxylic acid esters of testosterone wherein the cycloalkyl group contains 4–6 carbon atoms, preferably 6 carbon atoms, which cycloalkyl group is substituted, preferably at position 4, with a side chain containing 4–6 carbon atoms, together with pharmaceutically acceptable carrier, preferably an aqueous suspending medium, such as those well known in the art.

The new therapeutically active agents to which the present invention relates are testosterone 17β-esters of the formula where R is cyclobutyl, cyclopentyl or cyclohexyl and R' is a straight chain or branched alkyl group having 4–6 carbons. A testosterone ester of the above formula, or mixtures thereof, together with a pharmaceutically acceptable carrier form a suspension or solution suitable for use as an injectable therapeutic composition. For example, the ester can be dissolved in an acceptable oily medium, such as ethyl oleate, or suspended in an aqueous medium in the form of micronised particles or in the form of milled particles.

Representative examples of testosterone compounds of the above formula include:

I. testosterone 17β-3-n-hexylcyclobutanecarboxylate (a mixture of cis and trans isomers)

II. testosterone 17β-3-n-butycyclopentanecarboxylate (a mixture of cis and trans isomers), III. testosterone 17β-(trans-4-n-butyl)-cyclohexanecarboxylate,

IV. testosterone 17β-(cis-4-n-butyl)-cyclohexanecarboxylate,

V. testosterone 17β-(trans-4-n-pentyl)-cyclohexanecarboxylate,

VI. testosterone 17β-(trans-4-n-hexyl)-cyclohexanecarboxylate, and

VII. testosterone 17β-(cis-4-n-hexyl)-cyclohexanecarboxylate.

The presently preferred compounds are:

(III)

(V)

(VII)

DESCRIPTION OF THE PREFERRED EMBODIMENTS

The present invention relates to the testosterone 17β-esters of the formula:

where R is cyclobutyl, cylopentyl or cyclohexyl and R' is a straight chain or branched alkyl group having 4–6 carbons.

The esters of the present invention can be prepared by esterfication of testosterone which involves the initial conversion of the carboxylic acid to its unsymmetrical mixed anhydride by treatment with trifluoroacetic anhydride in benzene. Alternatively, the same can be prepared via the acid chlorides in the presence of pyridine.

The invention also relates to a method of using the compounds, together with a pharmaceutically acceptable carrier, for medical conditions for which androgen treatment is indicated. Included in these uses is the induction and maintenance of fertility suppression in male animals. The present invention can be used to inhibit spermatogenesis in human males by virtue of its inhibitory effect on pituitary gonadotrophins or in conjunction with steriodal estrogens or progestins, whose suppressive action on the synthesis and/or release of pituitary gonadotrophins is well known, to provide adequate circulating levels of testosterone and so preserve libido and potentia which can be adversely affected by these substances.

The preferred compounds, which require separation of conformational isomers, include testosterone 17β-(trans-4-n-butyl)cyclohexanecarboxylate, testosterone 17β-(trans-4-n-pentyl)cyclohexanecarboxylate and testosterone 17β-(cis-4-n-hexyl)cyclohexanecarboxylate. Preferred carriers include aqueous suspending vehicles, such as those well known in the art, although oily vehicles, such as ethyl oleate, sesame oil, cottonseed oil, olive oil, and arachis oil are also appropriate. The preferred crystal size when formulated as an aqueous suspension is 3–30 microns in diameter.

Specifically, in pharmaceutical preparations, the testosterone esters of the present invention can be formulated as a suspension in an acceptable aqueous medium such as:

benzyl alcohol 1.00 g
sodium carboxymethyl cellulose "50" 0.50 g
disodium hydrogen phosphate dihydrate 0.376 g
sodium dihydrogen phosphate dihydrate 1.495 g
water for injection to 100 ml.

When formulating the esters of this invention in aqueous suspension, different crystal sizes can be prepared. The range of particle sizes of the testosterone ester can be 1–50 microns, preferably 3–30 microns, in diameter. Such a formulation is particularly suitable for the esters in which R is cyclohexyl. Alternatively, the esters can be formulated as a 2% solution in ethyl oleate, such formulation being particularly suitable for the esters in which R is cyclobutyl.

Experiments in rats demonstrate androgenic activity for all compounds disclosed herein and, for the preferred compounds III, V and VII, duration and intensity at least twice that of testosterone enanthate and far greater than testosterone propionate.

Experiments in ovariectomized rhesus monkeys show a sustained elevation of testosterone and its metabolite dihydrotestosterone following a single intramuscular injection of compounds III, V and VII, far greater than that seen following similar treatment with testosterone enanthate standard. Compounds III, V and VII do not show initial high peaks of blood testosterone as does the standard, testosterone enanthate, and therefore the preferred embodiments of the invention provide a more physiologically and thus therapeutically acceptable means of androgen medication.

Based on these experiments, it is anticipated that compounds III, V and VII can provide physiologically effective blood levels of testosterone and dihydrotestosterone for periods in excess of 10 weeks following a single intramuscular injection of 100–400 mg in a microcrystalline aqueous suspension. However, the amount of testosterone ester injected can vary appreciably and ordinarily will be an amount sufficient to produce the desired result, for example, an amount effective in suppressing spermatogenesis in male animals, an amount which provides effective androgen replacement therapy in methods of fertility control in male animals where the production of androgenic hormones of the testis is comprised, and the like.

The following examples will serve to illustrate the syntheses of the compounds and the practice of the invention, but are not to be considered limiting.

EXAMPLE I

Testosterone 17β-(trans-4- n-butyl) cyclohexanecarboxylate (III)

Preparation 1: trans-4- n-butylcyclohexanecarboxylic acid (II).

boxylate (13) was added. The reaction mixture was heated at reflux for 16 hr and was then cooled to 20° C. Water (38 ml) was added and the mixture was re-heated to reflux for a further 24 hr. The resulting mixture was evaporated to a small volume and the residue was dissolved in water (115 ml). The solution was acidified using concentrated hydrochloric acid and the product was then extracted into dichloromethane (4×50 ml). The combined dichloromethane extracts were evaporated to give predominantly trans-4-n-butylcyclohexanecarboxylic acid (11, 45.6 g).

The crude trans isomer was crystallized repeatedly until pure trans-4-n-butylcyclohexanecarboxylic acid (11, 23.7 g, 99.5%; 23.6 g, 99%) was obtained, as a low-melting solid, m.p. 37–39° C.

Anal. calc'd. for $C_{11}H_{20}O_2$: C, 71.70; H, 10.94 Found:

4-n-butylbenzoic acid (8, 50 g, 0.28 mol) was dissolved in glacial acetic acid (250 ml ) and the solution was then autoclaved and hydrogented over platinum oxide (2.0 g) at 20° C. for 18 hr. at 5- p.s.i. The catalyst was filtered and the solution evaporated in vacuo to leave a solid residue of predominantly cis-4- n-butylcyclohexanecarboxylic acid (9, 50.89). The solid was dissolved in dry dichloromethane (250ml) containing N,N-dimethylformamide (1 ml). Thionyl chloride (72.69, 0.61 mol) was cautiously added over 30 min and the mixture was then heated at reflux for 3 hr. The resultant solution was cooled to 20° C., anhydrous ethanol (31.5 g, 0.69 mol) was carefully added and the mixture was then heated at reflux for 1 hr. The cooled solution was poured into water (400 ml) and the separated dichloromethane layer was evaporated to give mainly ethyl cis-4-n-butylcyclohexanecarboxylate (13, 56.4 g), as a viscous oil.

Sodium (7.5 g, 0.33 mol) was dissolved in anhydrous ethanol (200 ml) and ethyl cis-4-n-butylcyclohexanecar-

C, 72.00; H, 11.19.

Preparation 2: trans-4-n-butylcyclohexanecarboxylic acid chloride (12)

trans-4-n-butylcyclohexanecarboxylic acid (11) (2.2 g, 11.84 mmol) was dissolved in anhydrous benzene (10.0 ml) and the solution was placed under nitrogen and allowed to stir at room temperature. Oxalyl chloride (1.6 ml, 17.91 mmol) was added dropwise to the above solution with a syringe through a rubber septum. The solution was allowed to stir until gas evolution had ceased (ca. 30 min). The benzene and the excess oxalyl chloride were removed in vacuo under a stream of nitrogen with occasional warming Additional benzene (10.0 ml) was added and this process was repeated. The material was finally dried in vacuo at room temperature to yield 2.4 g (99%) of the acid chloride. The material was used directly without further purification. NMR $(CDCl_3) \delta 0.9$ (t, —$CH_3$), 1.33 (broad m), 1.9 (m(, 2.0 (m, C-4$\underline{H}$), 2.67 (t of t, C-1 $\underline{H}$, J =10 Hz, J' =3 Hz).

Method A

Method A

Preparation 3: Testosterone 17β-(trans-4-n-butyl) cyclohexanecarboxylate (III)

Method A:

Testosterone (7, 26.02 mg, 0.09 mmol) was dissolved in anhydrous benzene (1.0 ml) and pyridine (0.10 ml) under nitrogen. The trans-acid chloride (12, 27.52 mg, 0.135 mmol), dissolved in anhydrous benzene (0.5 ml), was added to the above solution. The reaction mixture was allowed to stir for 30 min under nitrogen. TLC (silica gel, EtOAc:hexanes(2:3)) of the reaction mixture showed no more starting material. Aqueous sodium hydroxide (0.05N, 3.0 ml) was added to the reaction mixture and the mixture was extracted with ether (3×5 ml). The ether layers were washed with saturated NaHCO$_3$ (2×), H$_2$O (1×) and brine (1×), then dried over Na$_2$SO$_4$. Evaporation of the solvent gave 40.90 mg of the crude ester. HPLC (μ orasil, 7.5% EtOAc:heptane, 1.0 ml/min, UV 240 nm) showed the crude material to be essentially pure and showed none of the cis ester as a contaminant. The crystalline product obtained was combined, recrystallized from methanol and dried in vacuo at room temperature. m.p. 131–133° C. [a]$_D^{25}$ +88 (CHCl$_3$); NMR(CDCl$_3$) δ0.83(s, 3H,C18-CH$_3$), 1.18(s, 3H, C19-CH$_3$), 4.63 (t, 1H,C—17H), 5.76(br.s., 1H C—4 H)IR (KBr),ν$_{max}$ 1725, 1680, 1620 cm$^{-1}$; MS m/e =454 M+.

Anal. calc'd. for C$_{30}$H$_{46}$O$_3$: C, 79.25; H, 10.20; Found =C, 79.14; H, 19.95. Confirmation of the trans 1,4-diequatorial conformer shown as the structure III for the chair form was obtained by the application of X-ray crystallography. A suitable crystal was obtained from methanol as transparent, colorless, rectangular crystals.

Method B

Trans-4-n-butylcyclohexanecarboxylic acid (11, 50.0 g, 0.27 mol) was added to a solution of trifluoroacetic anhydride (57.0 g, 0.27 mol) in dry dichloromethane (600 ml) and the resulting solution was stirred for 30 min. at 20° C. Testosterone (7, 78.3 g, 0.27 mol) was then added and the mixture was stirred for a further 2 hr at 20° C. After this period, water (500 ml) was added and the two layers were briskly stirred together for 15 min. The dichloromethane layer was separated and washed successively with saturated NaHCO$_3$ (2×250 ml) and then H$_2$O (250 ml). Evaporation of the solvent gave the crude testosterone ester (139.6 g), as an oil which solidified slowly on standing. The solid was dissolved in anhydrous ethanol (140 ml) by warming and the solution was then cooled to 5° C. and held at this temperature for 2 hr. The precipitated solid was filtered and recrystallised twice more from ethanol (70 ml and 80 ml) to give testosterone trans-4-n-butylcyclohexanecarboxylate (65 g, 99.1%) as a white crystalline solid, m.p. 132–134° C. It was identical with the sample prepared by means of Method A.

Example II

Testosterone 17β-(cis-4-n-butyl)cyclohexanecarboxylate (IV)

Preparation 1: cis-4-n-butylcyclohexanecarboxylic acid (9)

A solution of 4-n-butylbenzoic acid (8, 26.73 g, 0.15 mol) in acetic acid was hydrogenated in the presence of PtO$_2$ (0.4 g) at 50 psi until the uptake of hydrogen was complete. The catalyst was filtered and the solution evaporated in vacuo to leave a mixture of cis and trans-4-n-butylcyclohexanecarboxylic acids (predominently cis-4-n-butylcyclohexanecarboxylic acid). Esterification of the mixed acids with methanol-sulfuric acid afforded a mixture of methyl cis and trans-4-n-butylcyclohexanecarboxylates, (predominently cis). The mixture was separated by HPLC (Waters, Prep LC System 500) equipped with a single PrepPak/500 silica gel column using EtOAC:hexane (1:99) as the mobile phase at a flow rate of 100ml/min. The fast moving fraction was pure methyl cis-4-n-butycyclohexanecarboxylate (14).500 MHz PMR displayed a quintet at δ2.51 (d, J =3-4 Hz which is expected pattern for the equatorial C-1 methine proton adjacent to the carboxylate group. While the signal for axial C-1 methine of the trans isomer was found at δ2.27 as a clean triplet of triplet (J =10 Hz, J =3Hz). The slow moving fraction was purely methyl trans-4-n-butylcyclohexanecarboxylate. The difference between the retention times for the cis and trans methyl esters was ca. 1.0 minutes. The ratio of cis to trans separated was 7 to 3, weighing 23.4 g (87.5%).

The cis methyl ester (14, 500 mg) was dissolved in methanol (5 ml) and stirred in a nitrogen atmosphere. A solution of NaOH in aqueous methanol (5 ml; 2.4 g NaOH in 30 ml water which was then diluted to 100 ml with methanol) was added and the mixture stirred for 24 hr at room temperature. The methanol was evaporated, water added, and then extracted with heptane (3×). The aqueous fraction was acidified to approximately pH 4 with dilute HCl, saturated with NaCl, and extracted with EtOAC (3×). The EtOAC extract was washed with water and dried over Na$_2$O$_4$, then evaporated in vacuo to give the cis-carboxylic acid (9, 0.35 g). A small aliquot was esterfied with diazomethane and analyzed by HPLC. Less than 1% of the trans isomer was present. The reaction was repeated on the remaining 400 mg. A total of 626 mg of the cis acid was obtained.

Preparation 2: Testosterone 17β-(cis-4-n-butyl)cyclohexanecarboxylate (IV)

The cis-carboxylic acid (9, 0.626 g) was stirred in dry benzene (7 ml) and trifluoroacetic anhydride (0.49 ml) was added. The mixture was stirred 1 hr at room temperature and testosterone (7, 0.980 g) was added as a solid. The mixture was stirred an additional 45 min, diluted with ice-water and saturated NaHCO$_3$ solution, and extracted with benzene (3×). The benzene extract was washed with saturated NaHCO$_3$ solution (1×), H$_2$O (2×), brine (1×) and then dried over Na$_2$SO$_4$. The solvent was evaporated in vacuo to give crude IV (1.59 g). The residue was chromatographed on a dry silica gel column (4×80 cm) using ether:hexanes (2:1) as the developing solvent. Two fractions were isolated. These could not be purified by crystallization and were combined (1.015 g).

The mixture was chromatographed on a Prep-Pak/500 C$_{18}$ cartridge using acetonitrile as solvent. Collected fractions were analyzed by HPLC (Nova Pak C$_{18}$ column; methanol solvent; U.V. detector). A total of 0.45 g of 98% pure product was obtained. An additional 0.468 g of 90% pure product was rechromatographed as above. Before the material could be injected into the chromatograph, some crystalline material formed. The solution was cooled and the crystals were filtered. Analysis by HPLC as above showed the crystals, mother liquor, and original material to be identical (90:10 mixtures). All were combined and re-run on the preparative chromatograph. Good fractions were combined to give 0.17 g of 97% pure product. This was kept separate from the 98% pure product obtained above. The 98% pure fraction was crystallized from acetonitrile to give good cis ester (IV, 64.9 mg) m.p. 53.5-56° C. HPLC as above on the Nova Pak C$_{18}$ column showed the crystals and mother liquor to be identical.

The crystalline product was saved and physical data was run on the mother liquors. NMR (CDCl₃) δ0.83(s, 3H, 18-C$\underline{H}_3$), 1.17(s, 3H, 19-C$\underline{H}_3$), 4.67 (t, 1H, C-17 $\underline{H}$), 5.77(br.s.1H, C-4 $\underline{H}$); IR (Thin Film)$\nu_{max}$ 1725, 1675, 1620 cm⁻¹; MS: m/e =454 M⁺.

Analysis: Calc'd for C₃₀H₄₆O₃: C,79.25; H,10.20; Found: C,78.62; H,10.10.

EXAMPLE III

Testosterone 17β-(trans-4-n-pentyl)cyclohexanecarboxylate (V)

V

Preparation 1: trans-4-n-pentylcyclohexanecarboxylic acid (16)

This compound was prepared from 4-n-pentylbenzoic acid (15, 53.8 g, 0.28 mol), in a manner similar to the procedure described for trans-4-n-butylcyclohexanecarboxylic acid (11) in Example I, Preparation 1 in an overall yield of 80% (43 g); m.p. 50–51° C. (pet. ether).

Preparation 2: trans-4-n-pentylcyclohexanecarboxylic acid chloride (17)

In a dry system, the trans-acid (16, 14.21 g, 72.4 mmol) in anhydrous benzene (50 ml) was cooled in an ice bath and freshly distilled thionyl chloride (217.2 mmol) added dropwise. The mixture was stirred overnight at room temperature, the benzene removed in vacuo and three subsequent portions of benzene (80 ml) added and distilled out to remove excess thionyl chloride. The acid chloride (17) was used without further purification.

Preparation 3: Testosterone 17β-(trans-4-n-pentyl)cyclohexanecarboxylate (V)

Testosterone (7, 26.02 mg, 0.09 mmol) was dissolved in anhydrous benzene (1 ml) and pyridine (0.10 ml) under nitrogen. The trans-acid chloride (17, 29.26 mg, 0.135 mmol), dissolved in anhydrous benzene (0.5 ml), was added to the above solution. The reaction mixture was allowed to stir for 30 min under nitrogen. TLC (silica gel, EtOAc: hexane (2:3)) of the reaction mixture showed no more starting material. Aqueous NaOH (0.05N, 3.0 ml) was added to the reaction mixture and the mixture was extracted with ether (3×5 ml). The ether layers were washed with saturated NaHCO₃ (2×), H₂O (1×), brine (1×), and then dried over Na₂O₄. Evaporation of the solvent gave 42 mg of the crude ester. The crude product was recrystallized from ether-pet. ether to give 35.8 mg (85%) of white crystals: m.p. 135–137° C.; $[\alpha]_D^{25}$+89 (CHCl₃); IR, $\nu_{max}$ 1720, 1680; NMR (CDCl₃) δ(s, 3H, 18-C$\underline{H}_3$), 1.20 (s, 3H, 19-C$\underline{H}_3$); 4.66(t, 1H, 17-$\underline{H}$), 5.76(s, 1H, C-4 $\underline{H}$).

Anal. calc'd. for C₃₁H₄₈O₃: C, 79.49; H, 10.26; Found: C, 79.71; H, 10.44

EXAMPLE IV

Testosterone 17β-(trans-4-n-hexyl)cyclohexanecarboxylate (VI)

VI

Preparation 1: trans-4-n-hexylcyclohexanecarboxylic acid (19)

This compound was prepared from 4n-hexylbenzoic acid (18, 72.34 g, 0.28 mol), in a manner similar to the procedure described for trans-4-n-butylcyclohexanecarboxylic acid (11) in Example I, Preparation 1, in an overall yield of 60% (35.7 g), m.p. 30+C. (pet. ether).

Preparation 2: trans-4- n-hexylcylohexanecarboxylic acid chloride (20).

A solution of the trans-acid (19, 21.23 g, 0.1 mol), thionyl chloride (3.57 g, 0.3 mol) in anhydrous benzene (100 ml) was refluxed for 4 hr. The solvent was evaporated to give the crude acid chloride (20, 18.46 g, 80% yield) which was used directly without purification for the preparation of the ester.

Preparation 3: Testosterone 17β-(trans-4-n-hexyl)cyclohexanecarboxylate (VI)

To a stirred solution of testosterone (2.88 g, 0.01 mol) in pyridine (30 ml) at 0° C., under nitrogen, the acid chloride (20, 2.31 g, 0.03 mol) was added. After the addition was complete, the stirring was continued at room temperature for 20 hr. TLC (silica gel, CHCl₃ EtOAc (90:10)) of the reaction mixture at this time showed no more starting material. Aqueous NaOH (0.05N' 50ml) was added to the reaction mixture and the mixture was extracted with CHCl₃ (3×50 ml). The CHCl₃ layers were washed with saturated NaHCO₃ (2×), H₂O (1×), brine (1×), and then dried over Na₂SO₄. Evaporation of the solvent gave 43.45 g of the crude ester (VI). The crude product was recrystallized from acetonitrile to give a white amorphous solid; 41.0 g (85% yield), m.p. 95–98° C.; $[\alpha]_D^{25}$ +65 (CHCl₃); IR $\nu_{max}$, 1728, 1689; NMR (CDCl₃) δ0.85(s, 3H, 18-C$\underline{H}_3$), 1.20(s, 3H, 19-C$\underline{H}_3$), 4.40(t, 1H, 17-$\underline{H}$), 5.83(s, 1H, C-4 $\underline{H}$).

Anal. calc'd. for C₃₂H₅₀O₃: C, 79.83; H, 10.19; Found: C, 79.66; H, 10.32.

EXAMPLE V

Testosterone 17β-(cis-4-n-hexyl)cyclohexanecarboxylate (VII)

VII

Preparation 1: cis-4-n-hexylcyclohexanecarboxylic acid (21)

This acid (21) was prepared from 4-n-hexylbenzoic acid (18, 72.34g, 0.28 mol) in a manner similar to the procedure described for cis-4-n-butylcyclohexane-carboxylic acid (9) in Example II, preparation 1, in an overall yield of 80% of (47.6g).

Preparation 2: cis-4-n-hexylcyclohexanecarboxylic acid chloride (22)

A solution of the cis-acid (21, 21.23 g, 0.1 mol) thionyl chloride (3.57 g, 0.3 mol) in anhydrous benzene (100 ml) was refluxed for 4 hr. The solvent was evaporated to give the crude cis-acid chloride (22, 19.62 g, 85% yield) which was used directly without further purification for the preparation of the ester.

Preparation 3: Testosterone 17β-(cis-4-n-hexyl)cyclohexanecarboxylate (VII)

To a stirred solution of testosterone (2.88 g, 0.01 mol) in pyridine (30 ml) at a 0° C., under nitrogen, the acid chloride (22, 2.31 g, 0.03 mol) was added. After the addition was complete, the stirring was continued at room temperature for 24 hr. TLC (silica gel, $CHCl_3$ EtOAc (90:10)) of the reaction mixture at this time showed no more starting material. Aqueous NaOH (0.05N, 50 ml) was added to the reaction mixture and the mixture was extracted with $CHCl_3$ (3×50 ml). The $CHCl_3$ layers were washed with saturated $NaHCO_3$ (2×), $H_2O$ (1×), brine (1×), and then dried over $Na_2SO_4$. Evaporation of the solvent gave 4.6 g of the crude ester (VII). The crude product was recrystallized from ether to give white crystals 4.3 g (90% yield), m.p. 84-87° C.; $[\alpha]_D^{25}$ +98 ($CHCl_3$); IR, $\nu_{max}$ 1730, 1665; NMR ($CDCl_3$) δ0.85 (s, 3H, 18-$CH_3$), 1.20(s, 3H, 19-$CH_3$), 4.66(t, 1H, 17-H), 5.76(s, 1H, C-4H).

Anal. calc'd. for $C_{32}H_{50}O_3$: C, 79.67; H, 10.37 Found: C, 79.85; H, 10.15

Testosterone esters prepared according to the previous examples and evaluated for androgenic activity in the subsequent examples are set forth in Table 1.

TABLE 1

| Compd NO. | M.P.* | Name |
|---|---|---|
| I | 94-96 | Testosterone 17β-3-n-hexylcyclobutanecarboxylate (a mixture of cis and trans isomers) |
| II | 36-42 | Testosterone 17β-3-n-hexylcyclopentanecarboxylate (a mixture of cis and trans isomers) |
| III | 131-133 | Testosterone 17β-(trans-4-n-butyl)-cyclohexanecarboxylate |
| IV | 53.5-56 | Testosterone 17β-(cis-4-n-butyl)-cyclohexanecarboxylate |
| V | 125-127 | Testosterone 17β-(trans-4-n-pentyl)-cyclohexanecarboxylate |
| VI | 95-98 | Testosterone 17β-(trans-4-n-hexyl)-cyclohexanecarboxylate |
| VII | 84-87 | Testosterone 17β-(cis-4-n-hexyl)-cyclohexanecarboxylate |

*melting point, °C.

EXAMPLE VI

Figure 1:
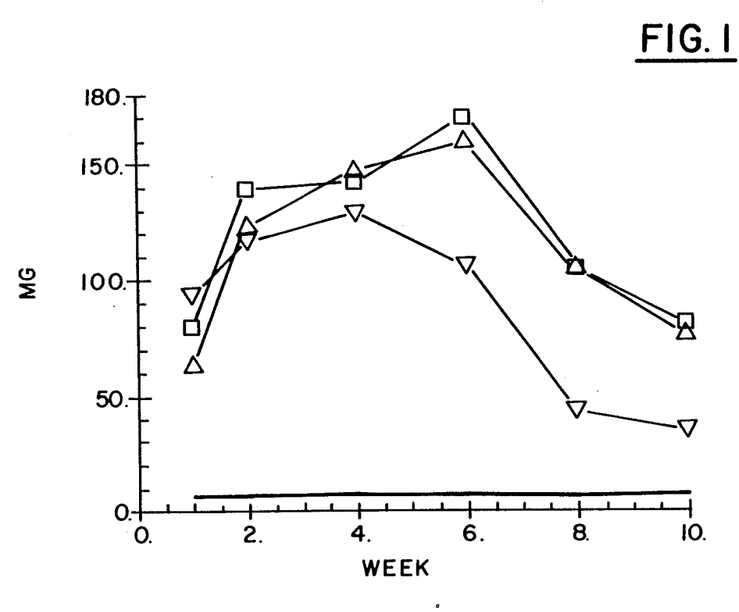
FIG. 1–5 and 8 Ventral prostate weight following a single subcutaneous injection of 2 mg of testosterone derivative to immature castrate male rats (n=5).
Figure 2:
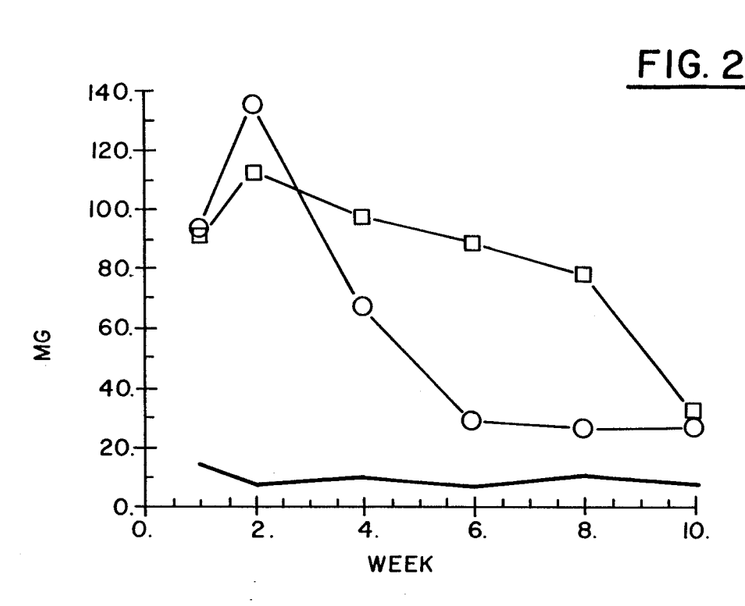
Figure 3:
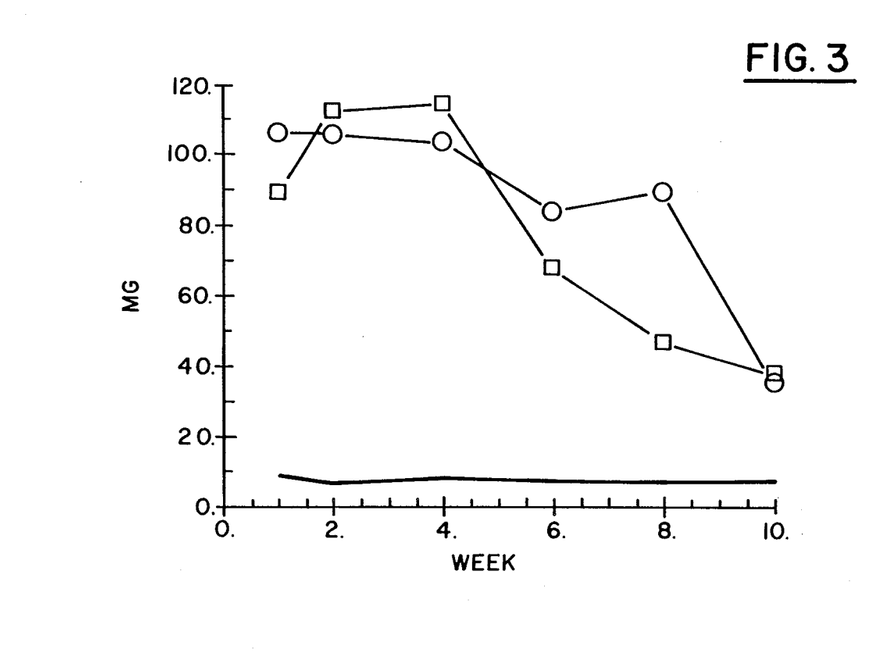
Figure 4:
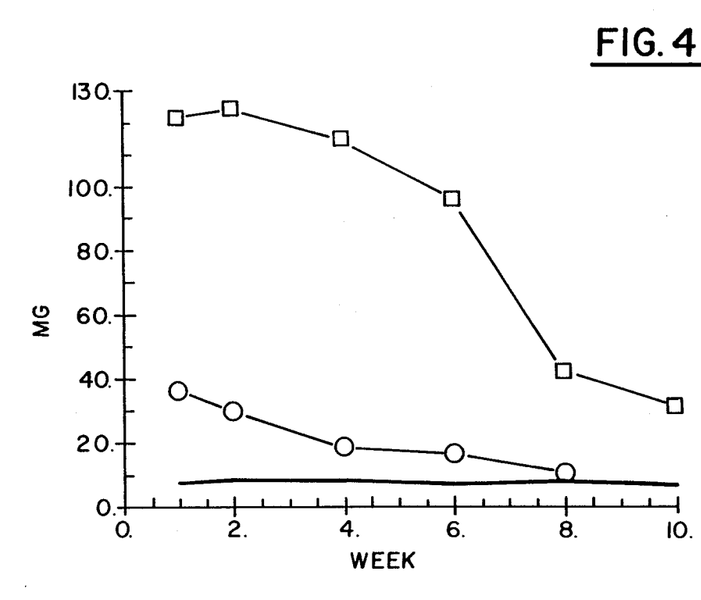
Figure 5:
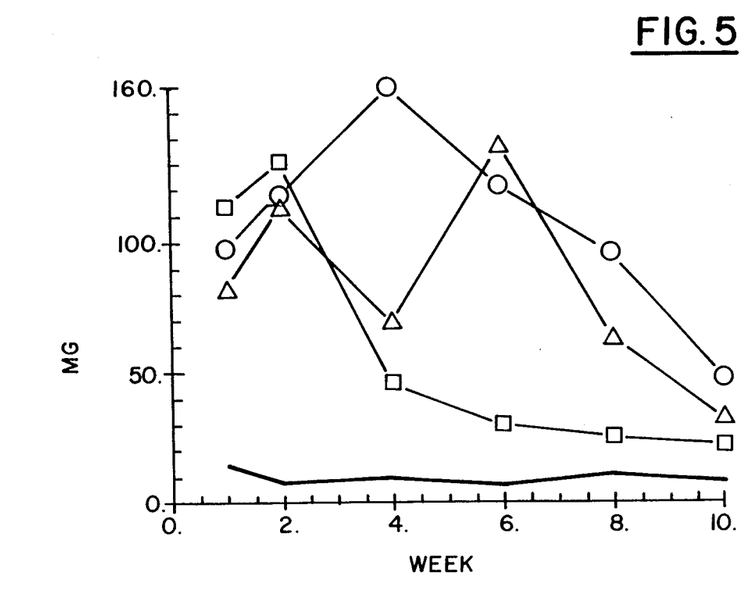

In studies designed to demonstrate intensity and duration of androgenic activity, the compounds in Table 1 were administered subcutaneously to immature, castrated male rats as micronized aqueous suspensions and/or ethyl oleate solutions. Five animals were sacrificed at 1, 2, 4, 6, 8 and 10 weeks following drug administration and seminal vesicles and ventral prostates removed, cleaned of adherent fat and connective tissue and weighed to the nearest 0.1 mg. Testosterone enanthate and testosterone propionate, dissolved in ethyl oleate (a commonly employed oily vehicle), were included as standards and aqueous suspending vehicle and ethyl oleate treated rats served as vehicle controls. The results of these studies for ventral prostate weight are found in FIGS. 1-5. In FIG. 1, the results for testosterone 17β-(trans-4-n- butyl) cyclohexanecarboxylate (aqueous suspension) are indicated by -□-, the results for testosterone 17β-(trans-4-n-pentyl) cyclohexanecarboxylate (aqueous suspension) are indicated by -▲-, the results for testosterone enanthate (ethyl oleate ) are indicated by -+-, and the solid line indicates the results for aqueous vehicle control. In FIG. 2, the results for testosterone 17β-3-n-hexylcyclobutanecarboxylate (cis/trans mixture) (aqueous suspension) are indicated by -O-, the results for testosterone enanthate (ethyl oleate) are indicated by -□-, and the solid line indicates the results for aqueous vehicle control. In FIG. 3, the results for testosterone 17β-3- n-butylcyclopentanecarboxlate (cis/trans mixture) (aqueous suspension) are indicated by -O-, the results for testosterone enanthate (ethyl oleate) are indicated by -□-, and the solid line indicates the results for aqueous vehicle control. In FIG. 4, the results for testosterone 17β-(cis-4-n-butyl) cyclohexanecarboxylate (ethyl oleate) are indicated by -O-, the results for testosterone enanthate (ethyl oleate) indicated by -□-, and the solid line indicates ethyl oleate vehicle control. In FIG. 5, the results for testosterone 17-β-(cis-4-n-hexyl) cyclohexanecarboxlate (aqueous suspension) are indicated by -O-, the results for testosterone enanthate (ethyl oleate) are indicated by -▲-, and the solid line indicates aqueous vehicle control. Compounds which were studied at the same time are shown on the same figure along with the standard, testosterone enanthate, and vehicle controls for that test. The standard and vehicle control groups were always included for each study. The results in, FIGS. 1-5 show the superior duration of activity for compounds III, V and VII respectively and, therefore, the preferred 6-carbon cycloalkyl group and substitution at position 4.

Figure 6:
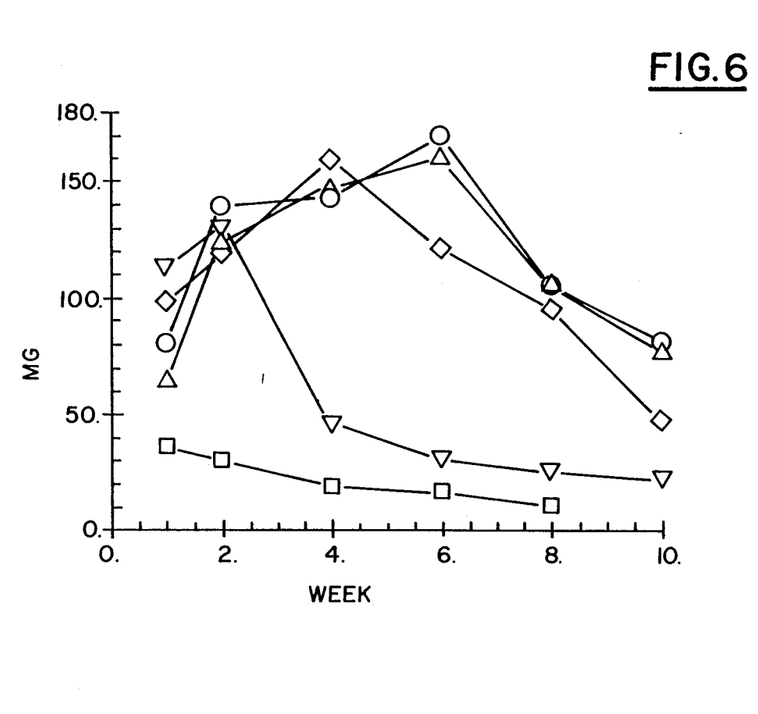
FIG. 6 Ventral prostate weight following a single subcutaneous injection of 2 mg of testosterone derivative to immature castrate male rats (n=5, combined tests).

Reference to FIG. 6 discloses that not only is the type of substitution on the cyclohexane ring important for duration and intensity of activity, but also their conformational isomerism. In FIG. 6, the results for testosterone 17β-(trans-4-n-butyl) cyclohexanecarboxylate (aqueous suspension) are indicated by -O-, the results for testosterone pb 17β-(cis-4-n-butyl) cyclohexanecarboxylate (ethyl Oleate ) are indicated by -□-, the results for testosterone 17β-(trans-4-n-pentyl) cyclohexanecarboxylate (aqueous suspension) are indicated by -▲-, the results for testosterone 17β-(trans-4-n-hexyl) cyclohexanecarboxylate (aqueous suspension) are indicated by -+-, and the results for testosterone 17β-(cis-4-n-hexyl) cyclohexanecarboxylate (aqueous suspension) are indicated by -◇-. Thus for the 4-n-butyl substitution, the trans form is more active while for the 4-n-hexyl, the cis form is superior.

The importance of the separation of conformational isomers is exemplified by compounds III and IV, the trans and cis isomers respectively, of testosterone 17β-(4-n-butyl)cyclohexanecarboxylate and by compounds VI and VII, the trans and cis isomers respectively, of testosterone 17β-(4-n-hexyl)cyclohexanecarboxylate. In the case of testosterone 17β-(4-n-butyl)cyclohexanecarboxylate, the trans isomer has a melting point of 131°-133° C. permitting formulation as an aqueous microcrystalline suspension and which, upon injection, was the most potent compound found. The corresponding cis isomer, compound IV, has a melting point of 53.5-50° C. which does not permit formulation as an aqueous microcrystalline suspension and which, upon injection in an oily vehicle, is far less potent than compound III prepared in either vehicle. To the contrary, the trans and cis isomers of testosterone 17β-(4-n-hexyl)cyclohexanecarboxylate had melting points closer together (95-98 and 84°-87° C., respectively) and both isomers could be formulated as aqueous microcrystalline suspensions, however, the cis isomer is the more potent. These findings teach that not only is the separation of conformational isomers important with respect to biological activity, but that compounds with melting points below approximately 70° C. cannot be micronized for preparation as microcrystalline aqueous suspensions, such formulations providing superior duration and intensity of androgenic activity for the preferred chemical compositions.

Figure 7:
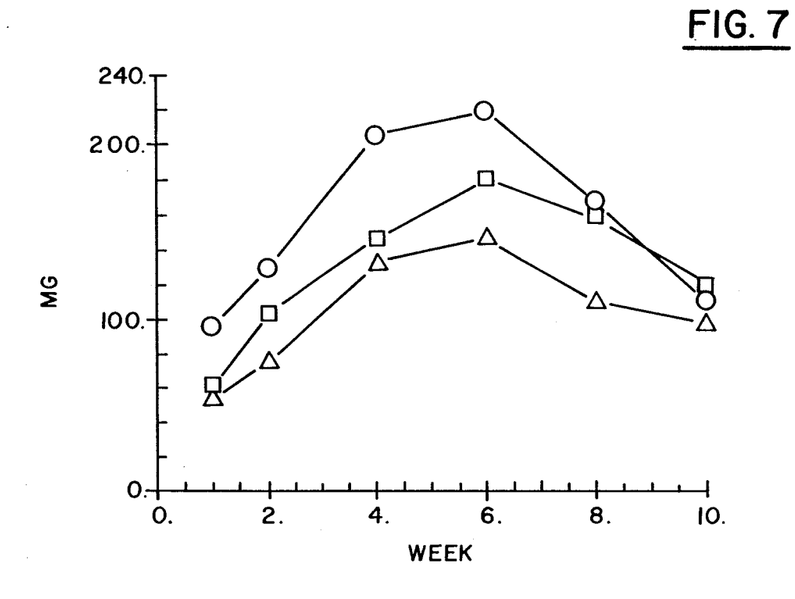
FIG. 7 Ventral prostate weight following a single subcutaneous injection of testosterone 17β-(trans-4-n-butyl)cyclohexanecarboxylate in aqueous suspension containing different particle sizes to immature castrate rats (n=5).

FIG. 7 shows the effect of particle size of compound III in aqueous suspension on duration and intensity of androgenic action. In FIG. 7, the results for particle size: 3-6 microns are indicated by -O-, the results for particle size: 20-30 microns are indicated by -□-, and the results for particle size: 40-50 microns are indicated by -△-.

These data support a preferred particle diameter range of 3-30 microns when the compound is administered as an aqueous crystalline suspension.

Figure 8:
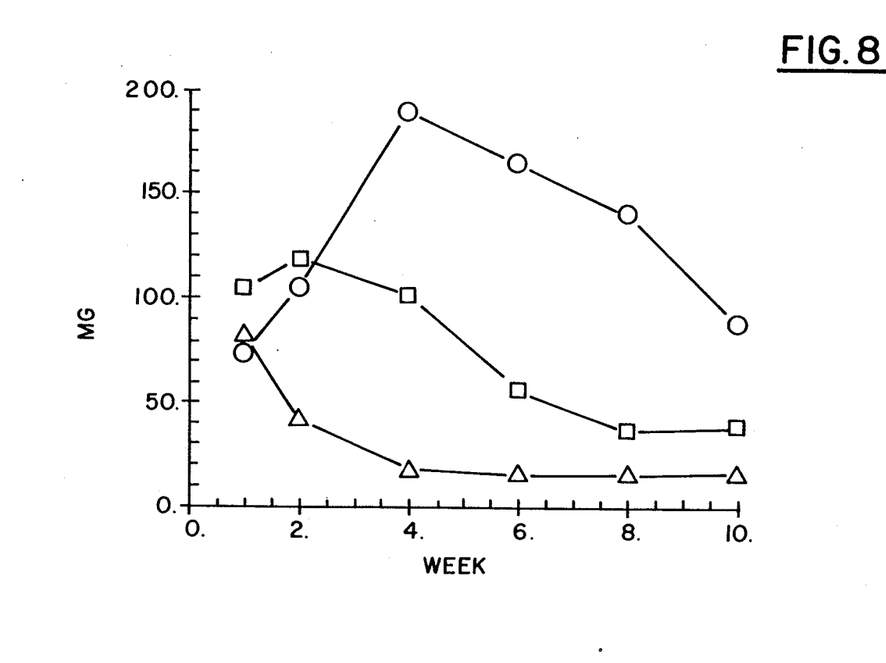

FIG. 8 compares the duration and intensity of activity following administration of compound III and testosterone enanthate and testosterone propionate standards. In FIG. 8, the results for testosterone 17β-(trans-4-n-buty l) cyclohexanecarboxylate (aqueous suspension) are indicated by -O-, the results for testosterone enanthate (ethyl oleate) are indicated by -□-, and the results for testosterone propionate (ethyl oleate) are indicated by -△-. While compound III was administered as an aqueous microcrystalline suspension, testosterone enanthate and testosterone propionate were administered in oily vehicle (ethyl oleate) because of their low melting points FIG. 8 not only shows the superiority of compound III over both standards, but also the weak activity of testosterone propionate. The superior duration and intensity of androgenic activity of the compounds of the present invention is evidenced by the comparison with the potent standard, testosterone enanthate.

EXAMPLE VII

Figure 9:
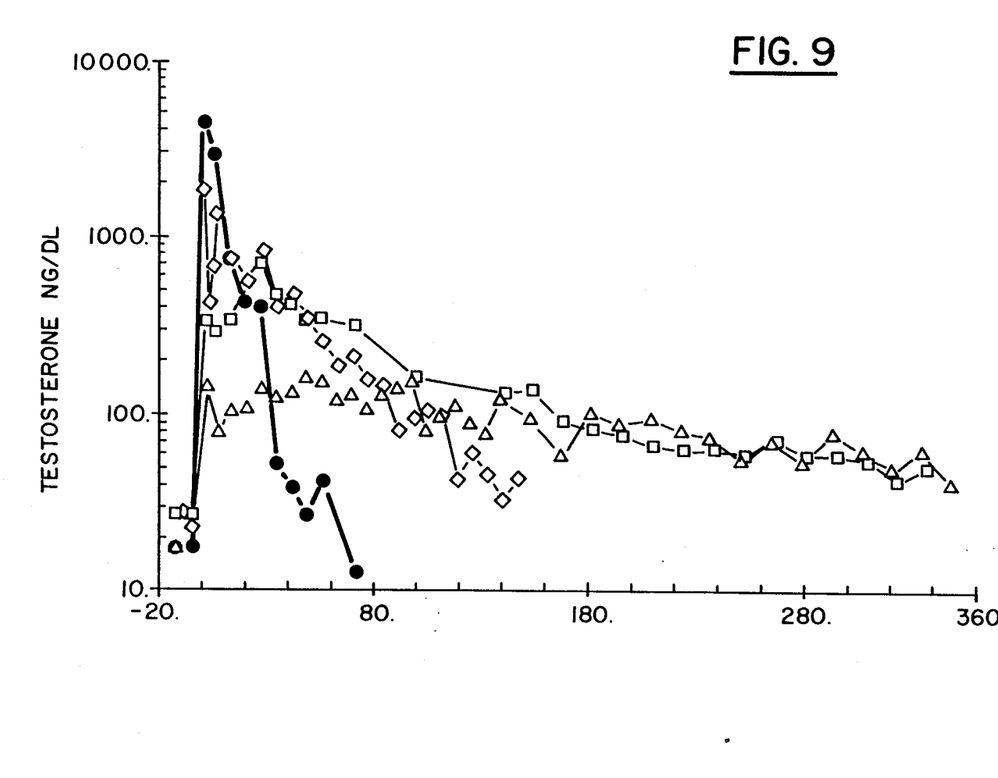
FIG. 9 Serum testosterone levels following a single intramuscelar injection of 40 mg of compounds III, V and VII and testosterone enanthate in orariectomized rhesus monkeys (n=5).
Figure 10:
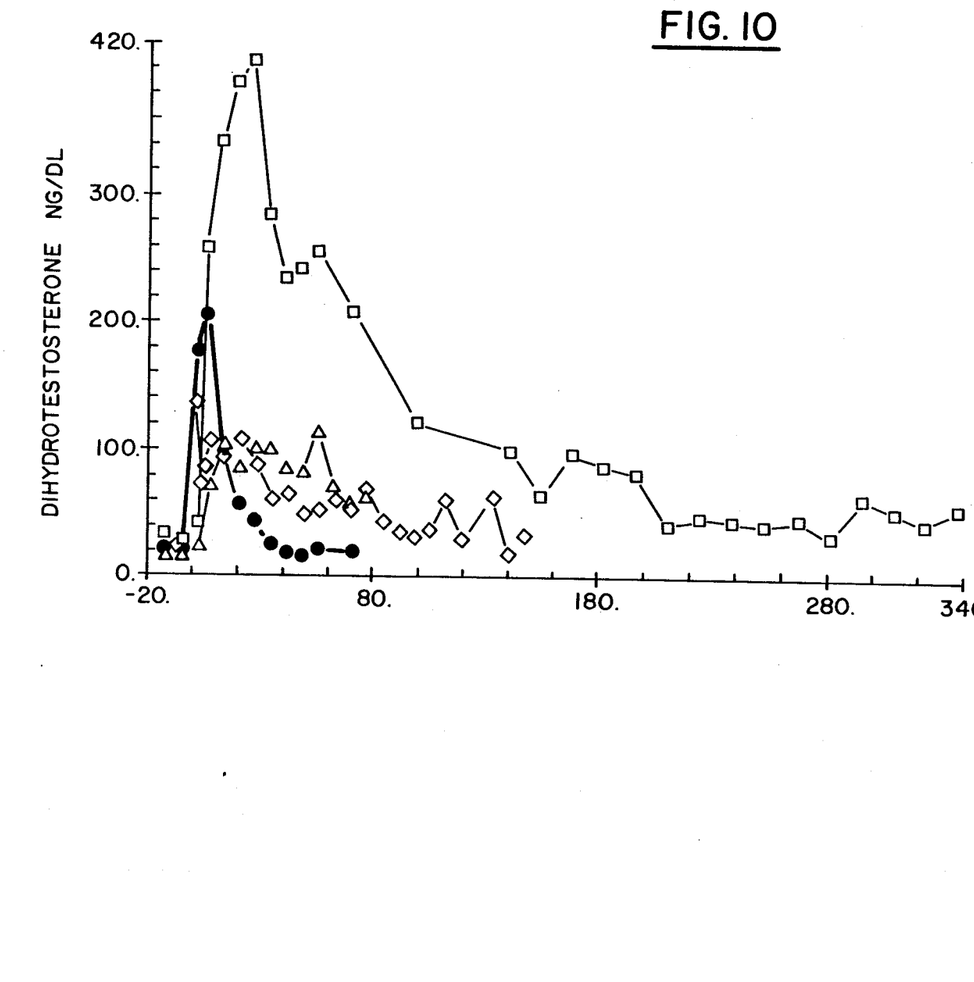
FIG. 10 Serum dihydrotestosterone levels following a single intramuscular injection of 40 mg of compounds III, V and VII and testosterone enanthate in orariectomized rhesus monkeys (n=5).

In order to further define the duration and intensity of these esters, several were administered to ovariectomized rhesus monkeys as a single intramuscular injection and blood samples were periodically withdrawn for the measurement of testosterone and its metabolite, dihydrotestosterone, by specific radioimmunoassay. The results of these studies are shown in FIGS. 9 and 10. In FIG. 9, the results for testosterone enanthate (ethyl oleate) are indicated by -●-, the results for testosterone 17β-(trans-4- n-butyl- cyclohexanecarboxlate (aqueous suspension) are indicated by -□-, the results for testosterone 17β-(trans-4-n-pentyl) cyclohexanecarboxlate (aqueous suspension) are indicated by -△-, and the results for testosterone 17β-(cis-4-n-hexyl) cyclohexanecarboxlate (aqueous suspension) are indicated by -◇-. In FIG. 10, the results for testosterone enanthate (ethyl oleate) are indicated by -●-, the results for testosterone 17β-(trans-4-n-butyl) cyclohexanecarboxylate (aqueous suspension) are indicated by -□-, the results for testosterone 17β-(trans-4-n-pentyl) cyclohexanecarboxylate (aqueous suspension) are indicated by -△-, and the results for testosterone 17β-(cis-4-n-hexyl) cyclohexanecarboxylate (aqueous suspension) are indicated by -◇-. It is known that these esters are rapidly hydrolyzed, once they have entered the circulation from the intramuscular depot, to testosterone, which is subsequently metabolized to dihydrotestosterone. Pretreatment blood levels of testosterone and dihydrotestosterone are low (see FIGS. 9 and 10) and the elevated levels of these hormones following drug administration is due to the rapid hydrolysis of the esters in blood. The radioimmunoassay employed does not recognize (cross-react with) the esters.

Reference to FIGS. 9 and 10 discloses not only the maintenance of physiological levels of testosterone and dihydrotestosterone for prolonged periods of time (approximately 10 weeks) following a single intramuscular injection of an aqueous suspension of 40 mg of compounds III, V and VII, but the absence of initial nonphysiological peak levels of testestosterone. The absence of such initial peak levels is of great importance in therapeutic medicine in that the patient is not exposed to high, nonphysiological levels of drug.

The foregoing invention has been described in some detail by way of examples for purposes of clarity and understanding. It will be obvious to those skilled in the art from a reading of the disclosure that various changes in form and detail can be made without departing from the scope of the invention.

We claim:

1. A cis or trans testosterone 17β-ester of the formula wherein R is cyclobutyl, cyclopentyl or cyclohexyl and R' is a straight chain or branched chain alkyl group of 4-6 carbons.

2. The testosterone ester according to claim 1 wherein said ester is testosterone 17β-3-n-hexylcyclobutanecarboxylate (a mixture of cis and trans isomers);

testosterone 17β-3-n-butylcyclopentanecarboxylate (a mixture of cis and trans isomers);

testosterone 17β-(trans-4-n-butyl)-cyclohexanecarboxylate;

testosterone 17β-(trans-4-n-pentyl)-cyclohexanecarboxylate;

testosterone 17β-(trans-4-n-hexyl)-cyclohexanecarboxylate; or testosterone 17β-(cis-4-n-hexyl)-cyclohexanecarboxylate.

3. The testosterone ester according to claim 2 wherein said ester is testosterone 17β-(trans-4-n-butyl)-cyclohexanecarboxylate; testosterone 17β-(trans-4-n-pentyl)-cyclohexanecarboxylate; or testosterone 17β-(cis-4-n-hexyl)cyclohexanecarboxylate.

4. A pharmaceutical composition comprising as an active ingredient at least one testosterone ester as claimed in claim 1 in an amount sufficient to exert a long-acting androgenic effect on male mammals together with a pharmaceutically acceptable carrier.

5. The composition according to claim 4 wherein said carrier is an aqueous suspending medium.

6. The composition according to claim 5 wherein said ester is in the form of micronised particles.

7. The composition according to claim 5 wherein said ester is in the form of milled particles.

8. The composition according to claim 5 wherein said ester present in said aqueous suspending medium has a particle diameter size of 3–30 microns.

9. The composition according to claim 4 wherein said carrier is an oily medium and said ester is dissolved therein.

10. The composition according to claim 9 wherein said carrier is selecting from the group consisting of ethyl oleate, peanut oil, and sesame oil.

11. The composition according to claim 4 wherein said pharmaceutically acceptable carrier is suitable for parenteral injection.

12. A method of providing long-acting androgenic therapy in male mammals comprising parenterally administering to male mammals said composition according to claim 4 in an amount and at a frequency sufficient to provide said long-acting therapy.

13. The method according to claim 12 wherein said amount and frequency of injection are sufficient to suppress spermatogenesis in male mammals.

14. The method according to claim 12 wherein said amount and frequency of injection are sufficient to provide effective androgen replacement therapy in methods of fertility control in male mammals, in which mammals the production of androgenic hormones of the testis is compromised.

15. The method according to claim 12 wherein said amount injected is in the range of about 100 to about 400 mg.

* * * * *